United States Patent [19]

Grubhofer

[11] Patent Number: 5,919,466

[45] Date of Patent: *Jul. 6, 1999

[54] METHOD FOR IMPROVING THE YIELD OF IMMUNOANTIBODIES IN THE VACCINATION OF ANIMALS AND HUMANS

[75] Inventor: Nikolaus Grubhofer, Kirchwald, Germany

[73] Assignee: GERBU Biotechnik GmbH, Gaiberg, Germany

[*] Notice: This patent is subject to a terminal disclaimer.

[21] Appl. No.: 08/816,787

[22] Filed: Mar. 19, 1997

Related U.S. Application Data

[63] Continuation-in-part of application No. 08/542,643, Oct. 13, 1995, and a continuation-in-part of application No. 08/130,645, Oct. 1, 1993, abandoned.

[30] Foreign Application Priority Data

Mar. 21, 1996 [DE] Germany ............... 196 11 235

[51] Int. Cl.$^6$ .................. A61K 45/00; A61K 39/00; A61K 47/00; C07K 16/00

[52] U.S. Cl. .................. 424/278.1; 424/184.1; 424/450; 530/388.1; 530/389.1

[58] Field of Search .................. 530/388.1, 389.1; 424/450, 287.1, 184.1

[56] References Cited

U.S. PATENT DOCUMENTS

| | | |
|---|---|---|
| 4,036,953 | 7/1977 | Adam et al. . |
| 4,082,735 | 4/1978 | Jones et al. . |
| 4,094,971 | 6/1978 | Chedid et al. . |
| 4,395,399 | 7/1983 | Ovchinnikov et al. . |
| 4,774,085 | 9/1988 | Fidler . |
| 4,845,042 | 7/1989 | Newman et al. . |
| 4,877,777 | 10/1989 | DiLuzio . |
| 4,880,634 | 11/1989 | Speiser . |
| 5,032,401 | 7/1991 | Jamas et al. . |
| 5,049,390 | 9/1991 | Wojdani . |
| 5,100,591 | 3/1992 | LeClef et al. . |
| 5,210,072 | 5/1993 | Chedid et al. . |
| 5,340,588 | 8/1994 | Domb . |
| 5,376,369 | 12/1994 | Allison et al. . |
| 5,409,698 | 4/1995 | Anderson et al. . |
| 5,538,733 | 7/1996 | Emery et al. . |
| 5,607,677 | 3/1997 | Jamas et al. . |
| 5,612,042 | 3/1997 | Jacobs . |
| 5,622,649 | 4/1997 | Hunter et al. . |
| 5,650,152 | 7/1997 | Anderson et al. . |
| 5,665,382 | 9/1997 | Grinstaff et al. . |
| 5,665,383 | 9/1997 | Grinstaff et al. . |
| 5,679,355 | 10/1997 | Alexander et al. . |
| 5,773,011 | 6/1998 | Grubhofer . |

FOREIGN PATENT DOCUMENTS

| | | |
|---|---|---|
| 0382271A1 | 8/1990 | European Pat. Off. . |
| 0399843A2 | 11/1990 | European Pat. Off. . |
| 4231675C2 | 7/1994 | Germany . |

OTHER PUBLICATIONS

Clough et al Inf. & Imm. 48/3:839–42, 1985.
Parant et al, Infectiion 13 (Suppl 2):S251–S255, 1985.
Riveau et al; J. Leukocyte Biology 44:448–54, 1988.
Solange, Chemistry & Physics of Lipids, 75:51–58, 1995.
Gregoriadis et al, Immunol Letters, 20:237–40, 1989.
Shimizu et al, Int. J. Immunopharmac. 14(8):1415–1420, 1992.
Yin et al, J. Biological Response Modifiers 8: 190–205, 1989.
Alam et al, Immunol Letters, 27: 53–58, 1991.
Allison et al, Tech. Adv. Vac. Development pp. 401–409, 1988.
Nesmeyanov et al, Biomed. Sci., 1(2):151–54, 1990.
Domkus et al. 5th Int'l Congress on Anti–Cancer Chemotherapy Poster #P517, 1995.
Byars et al, Vaccine 5:223–228, 1987.
Hilgers et al, Res. Immunol, 143: 494–503, 1992.
Mozes et al, PNAS, USA, 77(8): 4933–4937, Aug. 1980.
Shapira et al, Int. J. Immunopharmac. 7(5):719–723, 1985.
Ramasaney et al, J. Natl. Sci. Council, Sri Lanka, 21(1):125–140, 1993.
Amar et al, Mol. Immunol., 24(9):945–951, 1987.
Sharma et al Tech. Adv. Vaccine Development pp. 107–116 Alan R Liss Inc., 1988.
Grubhofer et al, FASEB Journal 8(4–5):A993, 1994.
Arakawa, Adv. Drug Del. Reviews, 10:1–28, 1993.
Grubhofer, Immunol Letters, 44:19–24, 1995.
Andronova et al, Colloq. INSERM 174(Forum Pept. 2nd, 1988):561–564, 1989.
Carelli et al Infection & Imm. 33(1):312–314, Jul. 1981.
Hilgers et al, Cellular Immunol, 90:14–23, 1985.
Hilgers et al, Cellular Immunol, 86:393–401, 1984.
Hilgers et al, Cellular Immunol. 92:203–209, 1985.
Hilgers et al, Int. Archs. All. Appl. Immunol 79:388–391, 1986.
Hilgers et al Int. Archs. All. Appl. Immunol 79:392–396, 1986.
Edelman et al, Intern. Rev. Immunol 7:51–66, 1990.
"A New Generation Of Softeners" published in the Journal for Theory, Technology and Application of Surfactants by Carl Hanser Verlag, München, Germany (Jan. 1993).
"Design and Evaluation of a Safe and Potent Adjuvant for Human Vaccines (MF59)" published in Vaccine Design: The Subunit and Adjuvant Approach, Chapter 10, by Gary Ott, Gail L. Barchfeld, David Chernoff, Ramachandran Radhakrishnan, Peter van Hoogevest and Gary Van Nest. (1995).

(List continued on next page.)

*Primary Examiner*—Nita Minnifield
*Attorney, Agent, or Firm*—Howard & Howard

[57] ABSTRACT

Immunological adjuvant containing GMDP (N-acetylglucos-aminyl-N-acetylmuramyl-L-alanyl-D-isoglutamine) and a colloidal, ultrafiltrable solution of solid, biodegradable lipids suitable as an additive in veterinary and human vaccines.

15 Claims, 1 Drawing Sheet

OTHER PUBLICATIONS

"A Comparison of Commercially Available Adjuvants for Use in Research" published in the Journal of Immunological Methods, by Beth Bennett, Irene J. Check, Margarent R. Olsen and Robert L. Hunter (1992).

"The Control of the Antibody Isotype Response to Recombinat Human Immunodeficiency Virus gp120 Antigen by Adjuvants" published in Aids Research and Human_viruses, vol. 8, No. 10, by R. Bomford, M. Stapleton, S.Winsor, A McKnight and T. Andronova (1992).

"Minimal Structural Requirements for Adjuvant Activity of Bacterial Peptidoglycan Derivatives" published in Biochemical and Biophysical Research Communications, vol. 59, No. 4, by Farielle Ellouz, Arlette Adam, Rita Ciorbaru and E. Lederer (1974).

"Antibody Formation and Sensitization with the Aid of Adjuvants" by Jules Freund, K. Jefferson Thomson, H.B. Hough, H.E. Sommer and T.M. Pisani (1948).

"The Mode of Action of Immunologic Adjuvants" by Jules Freund.

"Future Prospects for Vaccine Adjuvants" published in CRC Critical Reviews in Immunology, vol. 8, Issue 2, by H. Shaw Warren and Louis A. Chedid. (1988).

"The Adjuvant Activity of Nonionic Block Polymer Surfactants" published in the Journal of Immunology, vol. 133, No. 6, Dec. 1984, by Robert L. Hunter and Beth Bennett.

"An Adjuvant Formation That Selectively Elicits the Formation of Antibodies of Protective Isotypes and of Cell–mediated Immunity" published in the Journal of Immunological Methods, by Anthony C. Allison and Noelene E. Byars (1986).

"The Structure and Immunomodulating Function of Gluosaminylmuramyl Peptides" published in Sov. Medical Review D. Immunology, vol. 4, pp. 1–63, by Tatyana Andronova and Vadim Ivanov (1991).

Immunoadjuvant Activities of Synthetic N–Acetyl–Muramyl–Peptides or Amino Acids, published in Biken Journal, vol. 18, pp. 105–111, by Shozo Kotani, Yoshiro Watanabe, Fumio Kinoshita, Tsutomu Shimono, Ichijiro Morisaki, Tetsuo Shiba, Shoichi Kusumoto, Yuzo Tarumi and Kazuhiro Ikenaka (1975).

"Adjuvant Activity of 6–0–Acyl–Muramyldipeptides to Enhance Primary Cellular and Humoral Immune Responses to Guinea Pigs: Adaptability to Various Vehicles and Progenicity", published in Infection and Immunity, by Masachika Tsujimoto, Shozo Kotani, Fumio Kinoshita, Seizaburo Kanoh, Tetseuo Shiba and Shoichi Kusumoto (1986), 53(3):511–516.

"Adjuvant Formulation for use in Vaccines to Elicit both Cell–mediated and Humoral Immunity" published in Vaccine, vol. 5, by Noelene E. Byars and Anthony C. Allison (1987).

"A Compendium of Vaccine Adjuvants and Excipients" published in Vaccine Design, by Frederick R. Vogel and Michael F. Powell (1994).

"Adjuvants for Viral Vaccines" published in Reviews in Medical Virology, vol. 2, pp. 169–174, by R. Bomford (1992).

METHOD FOR IMPROVING THE YIELD OF IMMUNOANTIBODIES IN THE VACCINATION OF ANIMALS AND HUMANS

RELATED APPLICATIONS

This application is a continuation-in-part application of U.S. patent application Ser. No. 08/542,643 filed Oct. 13, 1995, which application was a continuation-in-part application of U.S. patent application Ser. No. 08/130,645 filed Oct. 1, 1993 now abandoned, which claims priority to German Application Serial No. 196 11 235.4 filed Mar. 21, 1996.

FIELD OF THE INVENTION

The present invention relates to immunological techniques and more specifically to the art of enhancing the natural response to veterinary and human vaccines by means of adjuvants.

BACKGROUND OF THE INVENTION

Vaccination against infectious diseases should lead to the formation of antibodies in the host organism which are sufficient for sustained or even lifelong protection. In the past this was very well accomplished simply by the administration of antigens in form of inactivated pathogen and it was relatively easy to manufacture commercial quantities of pathogenic bacteria or virus for the vaccines. The last decades however have witnessed the advent of viral infections such as hepatitis B and HIV where mass production of the antigen is not possible. One has to resort to genetically engineered viral subunits which are far less immunogenic than the whole pathogens and require repetitive application. Their high price is prohibitive for the badly needed mass vaccinations. Adjuvants, once mere laboratory items, thus have become the object of great medical and economic interest. Inspite of many efforts, a really efficient adjuvant admissible for contemporary medical and veterinary preventive medicine has not become available.

DESCRIPTION OF PRIOR ART

In 1948, Jules Freund (J. Immunol. 60, 383–98) introduced the idea of adjuvants and described its efficient realization. There is Freund's incomplete adjuvant (FIA), a mixture of mineral oil with commercial emulsifiers. To use it, one has to add an equal volume of aqueous antigen solution and force the mixture repeatedly through a syringe needle until a cream-like product appears which behaves like a water-in-oil emulsion, e.g. floats on a water surface. Injection together with the emulsion gives dramatically stronger immune responses than antigen alone. Adding killed mycobacteria to the emulsion, such as *M. tuberculosis* or *M. butyricum* further increases immunogenicity: This composition is called Freund's complete adjuvant (FCA), and in view of its phenomenal and general efficiency it would be ideal. However Freund's emulsion causes inulcerated and inflamed nodes (granulomas) at the injection sites which tend to burst open into suppurating abscesses, placing its use in preventive vaccines quite out of the question under modern standards. The only adjuvant presently admitted for human use is a fine suspension of aluminium hydroxide, the roots of which are even more archaic than those of Freund's (1926, A. T. Glenny et al. J. Pathol. 29, 31–40). It is based upon the assumption that antigens are somehow better recognized by the immune system when adsorbed to aluminium hydroxide. Aluminium hydroxide is much less effective than Freund's adjuvant and it too causes granulomas.

FURTHER TECHNOLOGICAL BACKGROUND

I have shown that the biocompatible GMDP glycopeptide (N-acetyl glucosaminyl-N-acetylmuramyl-L-alanyl-D-glutamine) is an excellent adjuvant in mice even in absence of any oil emulsion. The doses are only 1 $\mu$g GMDP/mouse (U.S. patent application Ser. No. 08/542,643). Surprisingly in larger animals such as rabbits, GMDP alone did not work as well as FCA. In this case apparently the mineral oil was required and I have shown that dimethyldioctadecylammonium chloride (DDA) was very effective as a replacement. The completely insoluble DDA could be dispersed when present in the form of an intimate solid mixture with zinc:L-proline complex which also furnished visible substance in the vials, moreover the zinc was believed to be a cofactor. DDA particles of 1–10 $\mu$m in size were formed. This formula was again at least as efficient as FCA and does not give any adverse symptoms: N. Grubhofer (1995) Immunology Letters 44, 19–24, U.S. patent application Ser. No. 08/504,409. The lipid dose for a rabbit is 100 $\mu$g, minuscule when compared with 100 mg oil per rabbit in Freund's. But in goats the attainable antibody titers again failed to measure up to FCA.

OBJECT OF THE INVENTION

It is the object of the present invention to propose an adjuvant formula suitable for larger animals and for humans. Moreover, it is an object of the present invention to provide a method and a formula of this kind which, besides increasing the immunogenic effect of an antigen (a vaccine) to the level obtainable with Freund's adjuvant, should consist solely of ingredients which are already officially admitted as parenteral drugs in order to facilitate practical use without delay.

BRIEF DESCRIPTION OF THE INVENTION

The invention is based on the surprising fact that, when using the optimum dose of glycopeptide together with the solid lipid substance present as a colloidal solution of submicron particles, the GMDP-lipid synergism which was discovered in smaller animals (U.S. patent application Ser. No. 08/505,409) can be retained in man-sized animals such as goats (40–60 kg).

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

BEST METHOD FOR CARRYING OUT THE INVENTION

Figure 1:
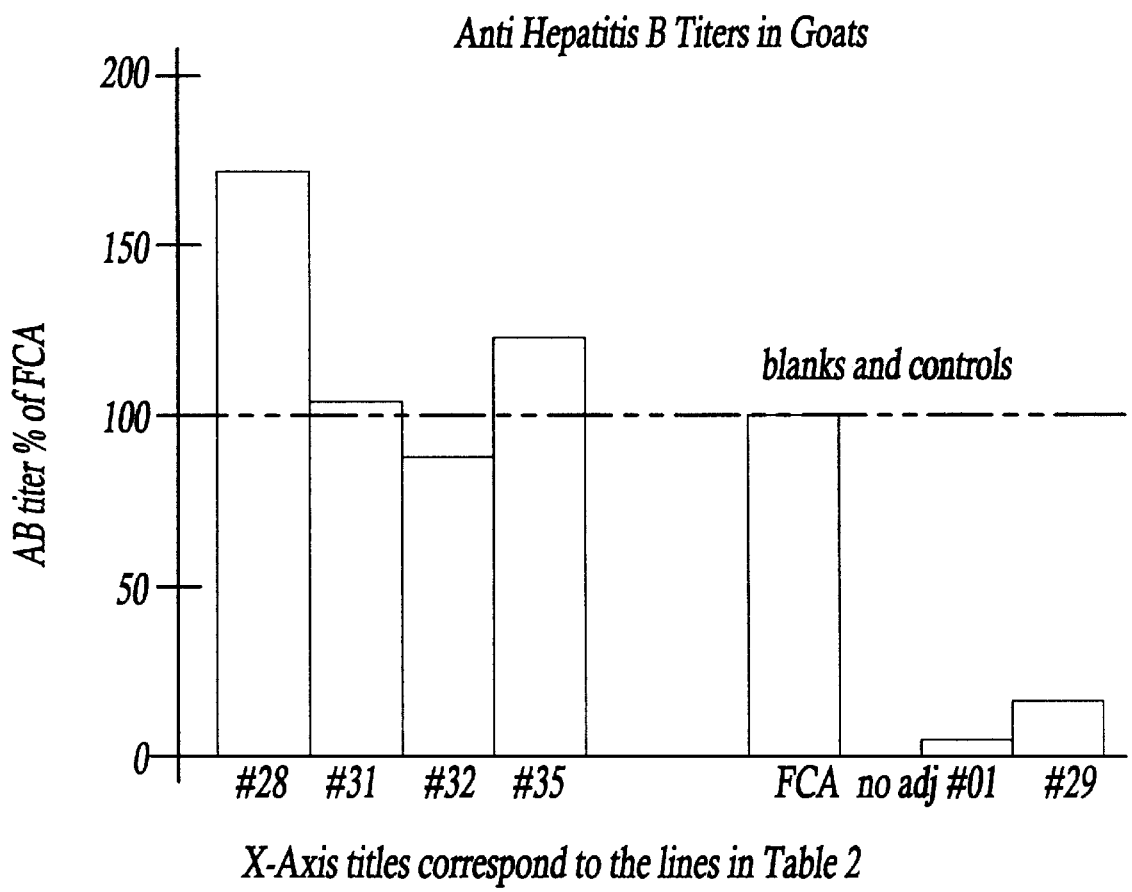
FIG. 1 is a graph illustrating results of the present invention.

The better results with Freund's adjuvant in larger animals most likely have to do with the outsized dose of oil emulsion. Considering a standard 2.5 mL injection of Freund's emulsion, a goat receives more than 1 g of mineral oil. Freund himself has already demonstrated (1948 loc.cit.) that excision of the immobile deposit of oil emulsion after a couple of hours does not considerably impair the immunostimulatory effect. This suggests that the plug of emulsion is actually useless and its effect really is due to a small portion of oil which can leak out fairly quickly and enters the host organism's lymphatic system, presumably in the form of very small droplets. At the same time more of the antigen becomes available, which otherways would remain buried within the bulk of the emulsion. It can be shown that this is indeed very probable: Freund's emulsion in contact with a medium such as bovine serum rapidly disintegrates into ultrafiltrable droplets upon gentle stirring, and the presence of such small droplets or particles could be the cause of the effect in Freund's adjuvant. See Example 1.

The mechanism of adjuvant action of particles, according to present consensus consists in being swallowed by macrophage-type blood cells and this opening up of the cells at the same time allows the antigen to enter them more easily, be it in physical or chemical connection with the particle, or independently. The small size of a particle is of advantage: easier phagocytosis, better mobility in the host organism making it possible to apply the necessary larger doses without giving rise to immobile plugs and concomitant granulomas. Furthermore the particle emulsions are more stable and the finished product can be sterilized by ultrafiltration.

Our developmental work therefore concentrated on improving the lipid part of the adjuvant. As a first step, the adjuvant effect of various formulations containing colloidal lipid solutions were studied without the presence of synergistic GMDP and therefore antibody titers are set in relation to those with Freund's incomplete Adjuvant(FIA). Experiments were carried out with sheep and goats and the results obtained in various stages of the work are summarized in TABLE 1. The lipids are present as colloidal solutions containing particles or droplets <0.2 μm in size obtained by mechanical microhomogenisation per Example 2.

TABLE 1

Adjuvant effect of colloidal lipid solutions. ANTIGEN: 100 μg

BSA. Animals: G: goat, S: sheep $A_{rel}$: Antibody titer at a given day divided by the antibody titer with FIA #15. Materials and methods are given in Examples 2–3. The solutions contain 30 g dextran and 10 L-proline per liter as solubilizers. Lipid dose: 50 mg/animal. Immunisations: Example 6 and 7.

|  | Lipid Adjuvant Substance | Emulsifier | Aggregate state | Animal | $A_{rel}$ 63 d |
|---|---|---|---|---|---|
| #1 | DDA | none | solid | G | 1.0 |
| #2 | Esterquat Hoe S 4039 | none | MP 40° C. | G | 1.4 |
| #3 | Lecithin from egg | none | solid | S | 0.5 |
| #4 | DL-α-Tocopherylacetate | Arlacel A | liquid | S | 0.7 |
| #5 | Lecithin/tocopherylacatat | none | MP 50° C. | G | 0.8 |
| #6 | Trioctanoin | Arlacel A | MP 9° C. | S | 0.0 |
| #7 | Tridodecanoin | Arlacel A | MP 45° C. | G | 0.7 |
| #8 | Paraffin oil DAB 10 | Arlacel A | liquid | S | 1.0 |
| #9 | Paraffin solid DAB 10 | Arlacel A | MP 60° C. | S | 1.3 |
| #10 | Silicone oil DC200 | Arlacel A | liquid | S | 1.5 |
| #11 | Tridodecanoin/cholesterol | Deoxycholate | solid | G | 0.9 |
| #12 | +Lecithin/tocopherylacetate + aluminiumhydroxide | none | solid | G | 0.9 |
| #13 | L 121 Blockpolymer | none | liquid | S | 0.3 |
| #14 | Polystyrene beads | Arlacel A | ~50 nm | G | 0.5 |
|  | Comparative tests and controls | | | | |
| #15 | Freund's incomplete adjuvant (FIA) | | | | 1.00 |
| #16 | Freunds M. butyricum-completed, (FCA) | | | | 2.6 |
| #17 | Aluminium hydroxide | | | | 0.2 |
| #18 | No adjuvant (blank) | | | | <0.1 |

The data presented in TABLE 1 are summarized and commented as follows:

1. Fine particles or droplets quite generally work as adjuvants regardless of chemical structure (#1–#14). One therefore is free to chose the most suitable ones under the various other aspects.
2. The lipid is best dosed around 50–100 mg per goat (~1 mg/kg). Unless applied as an ultrafiltrable solution, such high doses would deposit at the injection site, leading to premature enzymatic degradation and in humans to painful swelling.
3. Oils which are readily metabolized are much less effective than solid fats (#6 versus #7). This can only mean they are hydrolized too fast.
4. Solid lipids are more effective (#9 versus #8 or #10), due to their longer lifetime in the host, which gives them the chance to reach their target, presumably the macrophages and to stay there for a certain period. Improved stability of the solutions is an additional and important aspect of the use of solid lipids (Example 5)

DESCRIPTION OF THE PREFERRED EMBODIMENTS

These data establish the guidelines for further developmental work, and represent the essence of the claims in this invention. Ensuing immunisation tests with goats have lead to the results listed in TABLE 2. They prove that indeed the object of the invention has been achieved: an adjuvant formulation as effective as FCA in larger animals, but devoid of side effects and with the qualification as an auxiliary for human vaccines.

TABLE 2

Adjuvant effect of various formulations containing colloidal lipid solutions combined with GMDP. Antibody titers are set in relation to those with Freund's complete Adjuvant (FCA). Animals: Goats. ANTIGEN: Hepatitis B surface antigen: 20 μg/goat.

| Nr |  | GMDP/goat | Lipid/goat | Emulsifier | $A_{rel}$ d 63 |
|---|---|---|---|---|---|
|  | Lipid Adjuvant substance | | | | |
| #28 | Lecithin/Tocopherylacetate | 0.3 mg | 50 mg | none | 0.87 |
| #31 | Esterquat Hoe S4039 | 0.3 mg | 100 mg | none | 1.4 |
| #32 | Lecithin/Tocopherylacetate + 1 mg Alhydrogel | 0.3 mg | 100 mg | none | 1.0 |
| #35 | Tridodecanoin/Cholesterol | 0.3 mg | 120 mg | NaD | 1.2 |

-continued

| Nr | | GMDP/ goat | Lipid/ goat | Emulsi- fier | A$_{rel}$ d 63 |
|---|---|---|---|---|---|
| | Comparative tests and controls | | | | |
| #30 | Blank - no adjuvant | — | — | | <0.1 |
| #33 | Freunds complete adjuvant | | | | 1.00 |
| #01 | GMDP, no lipid | 0.3 mg | none | | <0.1 |
| #29 | no GMDP, lipid as in #28 | none | 50 mg | none | 0.13 |

A$_{rel}$ Antibody titer at day 63, divided by antibody titer with FCA # 33. and=Sodium deoxycholate. Hoe S4039 Di(stearoylhydroxyethyl)hydroxyethylmethylammonium chloride) prepared per Example 4. Materials and methods: Example 3. Immunisation: Example 7.

The data are also displayed in DRAWING 1.

The content of TABLE 2 is summarized and commented as follows:

1. The same level of efficiency as Freund's complete adjuvant has been reached by means of an adjuvant formulation containing GMDP and a lipid compound present in the form of an ultrafiltrable colloidal solution (#28–#35).
2. The synergistic interaction of GMDP with the lipid is clearly evident(# 01, #28, #29).
3. Aluminium hydroxide seems to increase effectivity (# 32).
4. The lipids are biodegradable compounds or mixtures thereof (#28–# 35)which are solid at body temperature, containing triglycerides, lecithin, cholesterol or tocopheryl acetate.
5. The lipids are self emulsifying and do not require additional emulsifiers. In some cases (# 35) sodium deoxycholate, a parenterally admitted emulsifier is helpful.
6. The value of quaternary ammonium salts is confirmed (# 31) especially of biodegradable analogs of DDA called esterquats compounds of great industrial importance as soft rinsing agents for laundry, with abundant toxicological data available, for instance Hoe S 4039. (1993 Puchta, et al. Tenside, Surf. Det. 30, 189–191). The esterquats are particulary promising as very potent adjuvant lipids for veterinary vaccines since they are non-toxic and biodegradable.
7. The lipids are dispersed by means of a hydraulic microhomogenizer to form stable colloidal solutions in the presence of stabilizing agents such as dextran or polyvinylpyrrolidone and L-proline. The resulting colloidal solutions contain solid lipid particles below 0.2 µm in diameter and can be filtered sterile.
8. The general principle developed here makes available many alternative formulations for further consideration and optimisation.
9. All goats were physically examined. They did not show signs of ill health or granuloma formations at the injection sites.
10. In human test with # 28 lecithin-tocopherylacetate no erythema, sensitivity or granuloma at the injection site is experienced.

EXAMPLE 1

Demonstration of the microdroplets obtainable from Freund's adjuvant emulsion.

Conventional FIA emulsion was prepared from 2 mL FIA (Difco Laboratories, Detroit Mich.# 0639-60) and 2 mL physiological saline by doing 20 double-strokes through a double-hub needle (#7979 micro-emulsifying needle 18×1⅞, Popper & Sons New Hyde Park N.Y. 11040). The resultant plug was placed on the surface of 100 mL fetal calf serum 37° C. which had been ultrafiltered to transparency. Upon gentle magnetic stirring most of the floating plug disappeared in the aqueous phase which became turbid. This turbidity easily passed through a 0.2 µm filter membrane.

EXAMPLE 2

Preparation of colloidal lipid solutions by means of a hydraulic homogenizer.

20 gr DDA (Genamin SC Hoechst AG, D-65920 Frankfurt), 2×recristallized from acetone (20 g/liter) was put into a solution of 30 g dextran 40 000 and 10 g L-proline warmed to 60° C. and stirred to homogenicity by means of a household blender. The resulting emulsion was transferred into the APV Gaulin Micron Lab 40 Homogenizer (APV Gaulin, D-23519 Lubeck, Ger.) and subjected to repeated cycles at 1000 bar (16000 psi) until it passed a 0.2 µm filter membrane. The dextran can be replaced by polyvinylpyrrolidone (Kollidon 17 PF , BASF D-67056 Ludwigshafen, Germany)

EXAMPLE 3

Preparation of the colloidal solutions used in the experiments.

3.1 The colloidal solution of DDA containing 20 mg/ml was used, as prepared in Example 2, injection 2.5 ml per goat.

3.2 Hoechst S4039, [Di(stearoylhydroxyethyl) hydroxyethylmethylammonium chloride), Hoechst AG, D-69520 Frankfurt), was purified as described in Example 4 and was used in the form of the concentrated suspension. The dextran-L-proline solution was made up in a higher concentration in order to reach the standard concentration after adding the necessary amount of S4039 suspension. The lipid was processed as in Example 2. Only 2–3 cycles were required through the APV machine at 1000 bar in order to make it pass through the 0.2 µm membrane.

3.3 Lecithin from egg, DAB 8 (Lipoid E 80, Lipoid GmbH Ludwigshafen), was processed as in Example 2.

3.4 DL-α-Tocopherylacetate, DAB 10, 85 parts and Arlacel A, 15 parts (ICI, Box 751 Wilmington, Del. 198987, USA) was processed as in Example 2.

3.5 Lecithin/DL-α-Tocopherylacetate 1/1 were dissolved in absolute ethanol and the ethanol evaporated. The resulting waxy mass started to melt at ca 45° C. and was processed without emulsifier as in Example 2.

3.6 Trioctanoin 99% , Sigma T 9001 Sigma Chem. Co., St. Louis Mo., 20 g and Arlacel A, 3 g as in Example 2. In this case it was necessary to cool the emulsion immediately after leaving the homogenizer in order to prevent creaming.

3.7 Tridodecanoin, a commercial cocoglyceride conforming to the USP XX and DAB 10 monographs for "hard fat" (Witepsol E 85, Hüls AG, D-45764, Marl) 20 g and Arlacel A, 2 g are processed as in Example 2. Cooling is necessary as in Example 3.6.

3.8 Paraffin oil „dünnflüssig" DAB 10 (E. Merck D-64271 Darmstadt) 20 g, and Arlacel A, 3 g as in Example 2.

3.9 Paraffin, point of solidification 54–56, E. Merck DAB 10, 20 g and Arlacel A, 3 g as in Example 2. Cooling is necessary as in Example 3.6.

3.10 Silicone oil DC200, 5 centistokes, Mr 770, Fluka # 85411 as sub 3.8 and in Example 2.

3.11 Tridodecanoin 90 parts was melted and 10 parts cholesterol (Fluka cholesterol from lanolin, #26740) dissolved in it with magnetic stirring and processed as in Example 2 after adding 5 parts sodium deoxycholate to give a 5% solution.

3.12 To 1 ml lecithin/D,L-α-tocopherylacetate colloidal solution prepared according to Example 3.7 add 0.05 ml Alhydrogel® (Superphos Biosector A/S). Of the mix 1.05 ml are used for one injection along with 100 μg BSA.

3.13 Blockpolymer L 121, (Synperonic L121 C. H Erbsl öh Düsseldorf, Germany) are processed as in Example 2.

3.14 Polystyrene, microspheres 0.1 μm obtained from Polysciences Inc Warrington Pa. USA (Polybead #00876, 2.5% suspension) and 2 mg Arlacel A /ml were dispersed and processed as in Example 2.

3.15 Freund's incomplete adjuvant was prepared according to Example 1 using 2.5 ml FIA and 2.5 ml phosphate buffered saline containing 100 μg BSA for one sheep or goat.

3.16 Freund's complete adjuvant Example 1 using FCA # 0639 Difco Labs. Detroit Mich., was processed as in Example 3.15

3.17 Aluminium hydroxide, Alhydrogel™ Superphos Biosector A/S was used. 10 ml of the commercial 2% suspension were incubated over night with 2 mg BSA, #3265-00, Intergen Comp. Purchase, N.Y. 10577) at room temperature in order to assocate the alumina with the protein (cf Erik B. Lindblad, Aluminium Adjuvants in The Theory and Practical Application of Adjuvants p 21–35, 1995 John Wiley & Sons Ltd D.E.S Stuward-Tull ed.). For the injection, 0.05 ml of the aluminium hydroxide-BSA suspension containing 1 mg aluminium hydrox-ide and 100 μg BSA was diluted to 5 ml.

3.28 Lecithin and tocopherylacetate was melted as in Example 3.5 and processed as in Example 2 to a concentration of 50 mg lipid/ml. GMDP was added to 0.3 μg/ml.

3.29 As # 3.28 but no GMDP added 3.31 As in Example 3.2. To the the colloidal solution adjusted to 40 mg/ml add 0.12 μg GMDP/ml and use 2.5 mL per goat immunization 3.32 As in 3.28: to 2 ml of the colloidal solution containing 50 mg lipid /mL add 0.05 ml aluminiumhydroxide suspension per ml.

3.33 FCA as in Example 3.16.

3.35 Tridodecanoin, 90 parts+cholesterol, 10 parts+ sodium deoxycholate, 5 parts as in Example 3.11, GMDP added to 0.12 μg/ml

EXAMPLE 4
Purification of HOE 4039

HOE S 4039 [Di(stearoylhydroxethyl)hydroxyethyl methylammonium chloride], Hoechst AG Frankfurt, is available as a commercial viscous liquid containing methosulfate anion and 15% isopropanol. The raw substance was purified by adding 230 g to 0.8 liter hot saline (20% NaCl) in a household blender and homogenizing slowly. The lipid floats, the liquid below is siphoned off. Washing with 20% brine is repeated 5 times. the floating cake is transferred into a dialysis tubing, squashed and dialyzed until only a trace of chloride can be detected in the outer liquid. An aliquot is evaporated to a soft, yellowish wax, MP~40–45° C. which is weighed for determination of lipid content in the main emulsion. The chlorine, sulfur and nitrogen content of the wax sample were subjected to analysis, the results indicating a min 98% exchange of the methosulfate counterion into chloride, the nitrogen content gave reasonable aggreement with chloride of the distearoyl compound. The bulk of the 12.5% emulsion was stored for use in adjuvant experiments.

EXAMPLE 5
Stability of microemulsion compared to stability of microsuspension.

Samples of colloidal solution 3.8 containing liquid paraffin and of the solution 3.9 containing solid paraffin were both stored at 45° C. over 2 weeks. Another set of samples was frozen over night and left at room temperature at daytime during 12 repeated cycles. The solution of liquid paraffin started creaming after some days under both treatments and could no longer be passed through 0.2 μm membranes. The solution of solid paraffin remained unchanged.

EXAMPLE 6
Immunisation of sheep

A solution of BSA (#3265-00, Intergen Comp. Purchase, N.Y. 10577) (100 μg ) in water was supplemented with colloidal lipid solution and with GMDP to yield 20 mg lipid and 150 μg GMDP and 100 μg BSA per animal. Injection at 4–6 sites subcutaneous. Booster injections with adjuvant and antigen were given after 14 and 28 days. At day 63 the sheep were bled and antibody titer assayed per ELISA.

EXAMPLE 7
Immunisation of goats

Hepatitis B surface antigen (International Enzyme Inc. Fallbrook Calif.) was exchanged for the BSA. All goats received 50 μg antigen and 300 μg GMDP and except in experiment #29, total injection volume was 5 mL distributed at 6 sites s/c. Immunusation schedule as in Example 6. The goat tests were performed at HTI Bioservice Inc in Ramona, Calif. 92065 USA

I claim:

1. A method for increasing the immune response of an animal or human to an antigen, said method comprising the steps of combining the antigen solution with the optimum dose of the glycopeptide GMDP (N-acetyl-glucosaminyl-N-acetylmuramyl-L-alanyl-D-isoglutamine) and a colloidal solution of sub-micron sized particles of a synergistic solid lipid substance without using emulsifiers; said synergistic solid lipid substance chosen from the group consisting of cholesterol, a paraffin a triglyceride lecithin DL-α-tocopheryl acetate, dimethyl distearoylhydroxyethyl ammonium chloride, or di(stearoylhydroxyethyl) hydroxyethylmethylammonium chloride; said synergistic solid lipid substance processed to produce said colloidal solution of sub-micron sized particles; and injecting the animal or human with the combination.

2. The method as claimed in claim 1 wherein the diameters of particles in the colloidal solution are below 0.2 μm.

3. The method as claimed in claim 1 further including sodium deoxycholate as an emulsifier.

4. The method as claimed in claim 1 further including aluminum hydroxide as a synergist.

5. The method as claimed in claim 1 further including dextran for stabilizing the colloidal lipid solutions.

6. The method as claimed in claim 1 further including polyvinylpyrrol-idone for stabilizing the colloidal lipid solutions.

7. The method as claimed in claim 1 further including L-proline for stabilizing and buffering the colloidal lipid solutions.

8. The method as claimed in claim 1 whereby the glycopeptide is used in a dose of 10 μg/kg body mass.

9. An adjuvant for increasing the immune response of an animal or human comprising:

An optimum dose of the glycopeptide GMDP (N-acetyl-glucosaminyl-N-acetylmuramyl-L-alanyl-D- isoglutamine); a colloidal solution of a solid lipid substance comprising particles having diameters below 1.0 μm, said solid lipid substance chosen from the group consisting of cholesterol, a paraffin, a triglyceride, lecithin, DL-α-tocopheryl acetate, dimethyl distearoylhydroxyethyl ammonium chloride or di(stearoylhydroxyethyl) hydroxyethylmethylammonium chloride; said adjuvant being added to an antigen solution for injection into an animal or human.

10. The adjuvant in accordance with claim 9 further including sodium deoxycholate as an emulsifier.

11. The adjuvant in accordance with claim 9 further including aluminum hydroxide as a synergist.

12. The adjuvant in accordance with claim 9 further including dextran for stabilizing the colloidal lipid solutions.

13. The adjuvant in accordance with claim 9 further including polyvinylpyrrolidine for stabilizing the colloidal lipid solutions.

14. The adjuvant in accordance with claim 9 further including L-proline for stabilizing and buffering the colloidal lipid solutions.

15. The adjuvant in accordance with claim 9, wherein the dose of glycopeptide selected amounts to 10 μg/kg of body mass.

* * * * *